United States Patent
Ruiter

(10) Patent No.: US 6,979,412 B2
(45) Date of Patent: Dec. 27, 2005

(54) METHOD OF PREPARING A COMPOUND CONCENTRATE AND PROCESSING SUCH A CONCENTRATE

(75) Inventor: David Ruiter, The Netherlands (NL)

(73) Assignee: Uniprox B.V., Mijdrecht (NL)

( * ) Notice: Subject to any disclaimer, the term of this patent is extended or adjusted under 35 U.S.C. 154(b) by 153 days.

(21) Appl. No.: 10/343,690

(22) PCT Filed: Jul. 30, 2001

(86) PCT No.: PCT/NL01/00584

§ 371 (c)(1),
(2), (4) Date: Apr. 8, 2003

(87) PCT Pub. No.: WO02/09521

PCT Pub. Date: Feb. 7, 2002

(65) Prior Publication Data

US 2003/0161891 A1     Aug. 28, 2003

(30) Foreign Application Priority Data

Aug. 2, 2000   (NL) .................................... 1015856

(51) Int. Cl.$^7$ ....................... C01B 15/037; A62D 3/00; A61K 33/40
(52) U.S. Cl. ................ 252/186.29; 252/186.28; 252/186.43; 252/182.29; 252/182.32; 424/616
(58) Field of Search .................. 252/186.28, 186.29, 252/186.27, 186.43, 182.29, 182.32; 424/616

(56) References Cited

U.S. PATENT DOCUMENTS

| 2,720,441 | A | * | 10/1955 | Wallace ........................ 8/111 |
| 4,839,156 | A | * | 6/1989 | Ng et al. ..................... 424/53 |
| 5,843,998 | A | * | 12/1998 | Song et al. ................. 514/588 |
| 5,846,570 | A | * | 12/1998 | Barrow et al. .............. 424/616 |
| 5,900,256 | A | * | 5/1999 | Scoville et al. ............ 424/616 |
| 6,025,431 | A | * | 2/2000 | Cardinali et al. ........... 524/547 |
| 6,387,858 | B1 | * | 5/2002 | Shah et al. ................ 510/161 |
| 6,458,340 | B1 | * | 10/2002 | Ibsen et al. .................. 424/53 |
| 6,555,020 | B1 | * | 4/2003 | Chadwick et al. ..... 252/186.26 |
| 2004/0033923 | A1 | * | 2/2004 | McClung .................... 510/302 |

FOREIGN PATENT DOCUMENTS

WO   WO 97/38582   10/1997

* cited by examiner

Primary Examiner—Joseph D. Anthony
(74) Attorney, Agent, or Firm—Darby & Darby

(57) ABSTRACT

The invention relates to a method of preparing a compound for the prevention of a contamination of raw materials, products, water and/or production means, which compound comprises at least hydrogen peroxide, glycerol and glycol acid, and wherein a mixture of glycerol and glycol acid is added to the hydrogen peroxide. The glycerol and glycol acid are combine and stirred while admixing a stabilizer for peroxide mixtures to form a stable gel-like concentrate, and subsequently when required, the concentrate is added in its entirety to the hydrogen peroxide in a previously determined ratio in order to form the compound.

6 Claims, No Drawings

METHOD OF PREPARING A COMPOUND CONCENTRATE AND PROCESSING SUCH A CONCENTRATE

This is a U.S. national phase application under 35 U.S.C. §371 of International Patent Application No. PCT/NL01/00584, filed Jul. 30, 2001, and claims the benefit of Dutch Patent Application No. 1015856, filed Aug. 2, 2000. The International Application was published in English on Feb. 7, 2002 as WO 02/09521 A2 under PCT Article 21(2).

The invention relates to a method of preparing a compound for the prevention of a contamination of raw materials, products, water and/or production means, which compound comprises at least hydrogen peroxide, glycerol and glycol acid, and wherein a mixture of glycerol and glycol acid is added to the hydrogen peroxide.

Such a method is known from the Dutch patent 1003316 in the name of applicant.

In the known method the compound is prepared from at least hydrogen peroxide, glycerol and glycol acid, wherein a solution of the glycerol and a solution of glycol acid is mixed and this mixture is added dropwise to a solution of hydrogen peroxide under conditions such that the solution of hydrogen peroxide maintains a temperature of 7° C., and preferably less than 4° C. The ratio hydrogen peroxide, glycerol and glycol acid to be applied is described extensively in said patent 1003316, so that for the sake of brevity reference is made thereto.

It is known that particularly in warmer regions a suitable disinfection method and compound are of great importance. A disadvantage of the compound disclosed in the Dutch patent 1003316 is that when production does not take place locally, large amounts of the aqueous compound obtained by the prior art method have to be transported, which involves high transport costs. This problem is not only inherent to the compound obtained according to the method of the Dutch patent 1003316, the invention of which dates back to 1996. The problem applies to the same extent to the product obtained in accordance with the European patent application EP-A-0 603 329, the invention of which dates back to 1991.

The primary objective of the inventors of the product proposed according to the Dutch patent 1003316 is the adaptation of the method such as to cut the aforementioned high transport costs.

Another object of the invention is to combat the explosive character associated with the known production method of the compound.

According to the invention the method of preparing a compound for the prevention of a contamination of raw materials, products, water and/or production means is characterized in that the glycerol and the glycol acid are combined and stirred while admixing a stabilizer for peroxide mixtures to form a stable gel-like concentrate, and in that subsequently when required, the concentrate is added in its entirety to the hydrogen peroxide in a previously determined ratio, in order to form the compound.

Surprisingly it has been found that in the method according to the invention there is no need at all for the concentrate to be added dropwise to the hydrogen peroxide while maintaining a temperature of below 7°, and preferably below 4°, as is required in the prior art.

On the contrary, in accordance with the invention the method is preferably performed such that prior to being added to the hydrogen peroxide, the concentrate has a temperature of approximately 20° C. This promotes proper and quick mixing to obtain the desired compound.

It is further preferred that the glycerol and the glycol acid be combined and subsequently stirred for at least 7 minutes while the stabilizer is being added, until the concentrate is clear and homogeneous. This is a simple, reproducible and reliable manner for obtaining the concentrate that is suitable for transport from a central location of preparation to a particular location where it is incorporated for the formation of the final compound. This aspect provides the key to the reduction of the considerable transport costs known from the prior art method. For the formation of the concentrate it is further desirable that prior to combining the glycerol and the glycol acid, they both have a temperature ranging from 18–24° C. The maintenance of this temperature promotes mixing due to the fact that glycerol and glycol acid then have a suitable viscosity value.

As will be clear from the foregoing, the invention is also embodied in the concentrate as such, which is characterized in that the same comprises at least glycerol, glycol acid and a stabilizer for peroxide mixtures while being substantially free of hydrogen peroxide.

The invention is further embodied in the processing of this concentrate for the preparation of a compound for the disinfection of raw materials, products, water and/or production means, wherein the concentrate is added in its entirety at a previously determined quantity of hydrogen peroxide for the formation of the compound.

The concentrate according to the invention may, for example, comprise the following components:
a) glycol acid in a 57% concentration for 31.25/100 parts;
b) stabilizer for peroxide mixtures for 6.25/100 parts; and
c) glycerol in pharmaquality USP 1.26 for 62.5/100 parts.

For the production of the compound for the prevention of a contamination of raw materials, products, water and/or production means, the thus obtained concentrate is to be added to hydrogen peroxide. To this end, for example, 8% by weight of concentrate may be added to 92% by weight of a 50% hydrogen peroxide solution.

What is claimed is:

1. A method of preparing a contaminated prevention formulation comprising the steps of:
   (a) mixing glycerol and glycol acid to form a mixture,
   (b) mixing the mixture with a stabilizer for peroxide to form a stable gel-like concentrate, and
   (c) adding the concentrate to hydrogen peroxide, wherein the concentrate and hydrogen peroxide are not cooled below ambient temperature.

2. The method of claim 1, wherein prior to step (a), glycerol is at a temperature ranging from 18–24° C.

3. The method of claim 1, wherein the mixture is stirred for at least 7 minutes while the stabilizer is being added.

4. The method of claim 1, wherein the concentrate is clear and homogenous.

5. The method of claim 1, wherein the concentrate is added to the hydrogen peroxide in its entirety.

6. The method of claim 1, wherein the temperature of the concentrate prior to being to the hydrogen peroxide is approximately 20° C.

* * * * *